(12) United States Patent
Surace

(10) Patent No.: US 10,695,530 B1
(45) Date of Patent: Jun. 30, 2020

(54) METHODS, DEVICES, SYSTEMS, AND KITS FOR REGULATING SKIN TEMPERATURE FOR MAMMALS TO INDUCE AND/OR MAINTAIN SLEEP

(71) Applicant: Slumber Science LLC, Sunnyvale, CA (US)

(72) Inventor: Kevin Surace, Sunnyvale, CA (US)

(73) Assignee: Slumber Science LLC, Sunnyvale, CA (US)

( * ) Notice: Subject to any disclaimer, the term of this patent is extended or adjusted under 35 U.S.C. 154(b) by 0 days.

(21) Appl. No.: 16/436,763

(22) Filed: Jun. 10, 2019

(51) Int. Cl.
*A61M 21/02* (2006.01)
*A61M 21/00* (2006.01)

(52) U.S. Cl.
CPC ..... *A61M 21/02* (2013.01); *A61M 2021/0066* (2013.01); *A61M 2205/364* (2013.01); *A61M 2205/3606* (2013.01); *A61M 2205/366* (2013.01); *A61M 2205/3613* (2013.01); *A61M 2205/3673* (2013.01); *A61M 2210/0606* (2013.01)

(58) Field of Classification Search
CPC ... A61F 2007/0007; A61M 2021/0066; A61M 2021/0083; A61M 21/02; A61M 2205/3368; A61M 2210/06
See application file for complete search history.

(56) References Cited

U.S. PATENT DOCUMENTS

| | | |
|---|---|---|
| 3,548,415 A | 12/1970 | Waters |
| 3,889,684 A | 6/1975 | Lebold |
| 4,381,025 A | 4/1983 | Schooley |
| 4,470,263 A | 9/1984 | Lehovec et al. |
| 4,483,021 A | 11/1984 | McCall |
| 4,854,319 A | 8/1989 | Tobin |
| 5,119,513 A | 6/1992 | McKay |
| 5,353,605 A | 10/1994 | Naaman |
| 5,623,828 A | 4/1997 | Harrington |
| 5,800,490 A | 9/1998 | Patz et al. |
| 5,867,999 A | 2/1999 | Bratton et al. |
| 6,297,728 B1 | 10/2001 | Rippbauer |
| 6,402,776 B1 | 6/2002 | Martin |
| 7,156,867 B2 | 1/2007 | Lennox |
| 8,236,038 B2 | 8/2012 | Nofzinger |
| 8,267,983 B2 | 9/2012 | Rogers et al. |
| 8,425,583 B2 | 4/2013 | Nofzinger |
| 8,529,613 B2 | 9/2013 | Radziunas et al. |
| 9,089,400 B2 | 7/2015 | Nofzinger |

(Continued)

FOREIGN PATENT DOCUMENTS

WO 2014078630 A1 5/2014

*Primary Examiner* — Christine H Matthews
(74) *Attorney, Agent, or Firm* — Hoge, Fenton, Jones & Appel, Inc.; Amy J. Embert

(57) ABSTRACT

A subject's forehead, and underlying pre-frontal cortex may be cooled by positioning a pre-cooled heat transfer pack on the subject's forehead so that the heat transfer pack is in thermal communication with the subject's forehead, the temperature of the pre-cooled heat transfer pack being below 10° Celsius. Thermal communication between the subject's forehead and the heat transfer pack may be maintained for a period of time sufficient to cool the subject's pre-frontal cortex. Cooling of the pre-frontal cortex may slow the metabolic rate of the subject's pre-frontal cortex and/or induce an onset of sleep for the subject.

21 Claims, 13 Drawing Sheets

(56) References Cited

U.S. PATENT DOCUMENTS

| | | |
|---|---|---|
| 9,211,212 B2 | 12/2015 | Nofzinger et al. |
| 9,492,313 B2 | 11/2016 | Nofzinger |
| 9,669,185 B2 | 6/2017 | Nofzinger |
| 10,058,674 B2 | 8/2018 | Walker et al. |
| 2007/0250138 A1 | 10/2007 | Nofzinger |
| 2009/0054958 A1 | 2/2009 | Nofzinger |
| 2010/0005572 A1 | 1/2010 | Chaplin |
| 2011/0125238 A1 | 5/2011 | Nofzinger |
| 2013/0019611 A1 | 1/2013 | Sims et al. |
| 2013/0238063 A1 | 9/2013 | Nofzinger |
| 2014/0137569 A1 | 5/2014 | Parish et al. |
| 2014/0312834 A1 | 10/2014 | Tanabe et al. |
| 2015/0018905 A1 | 1/2015 | Nofzinger et al. |
| 2015/0238725 A1* | 8/2015 | Tucker .................. A61M 21/02 600/26 |
| 2015/0290420 A1 | 10/2015 | Nofzinger |
| 2016/0128864 A1 | 5/2016 | Nofzinger et al. |

\* cited by examiner

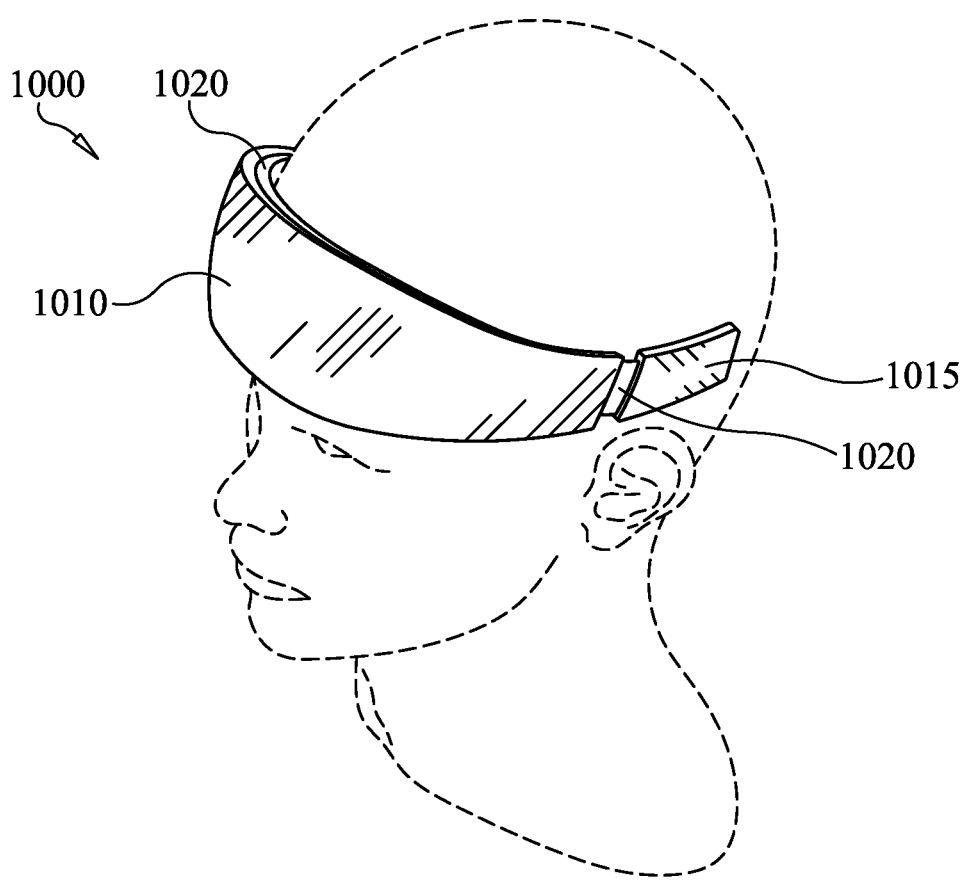
FIG. 12
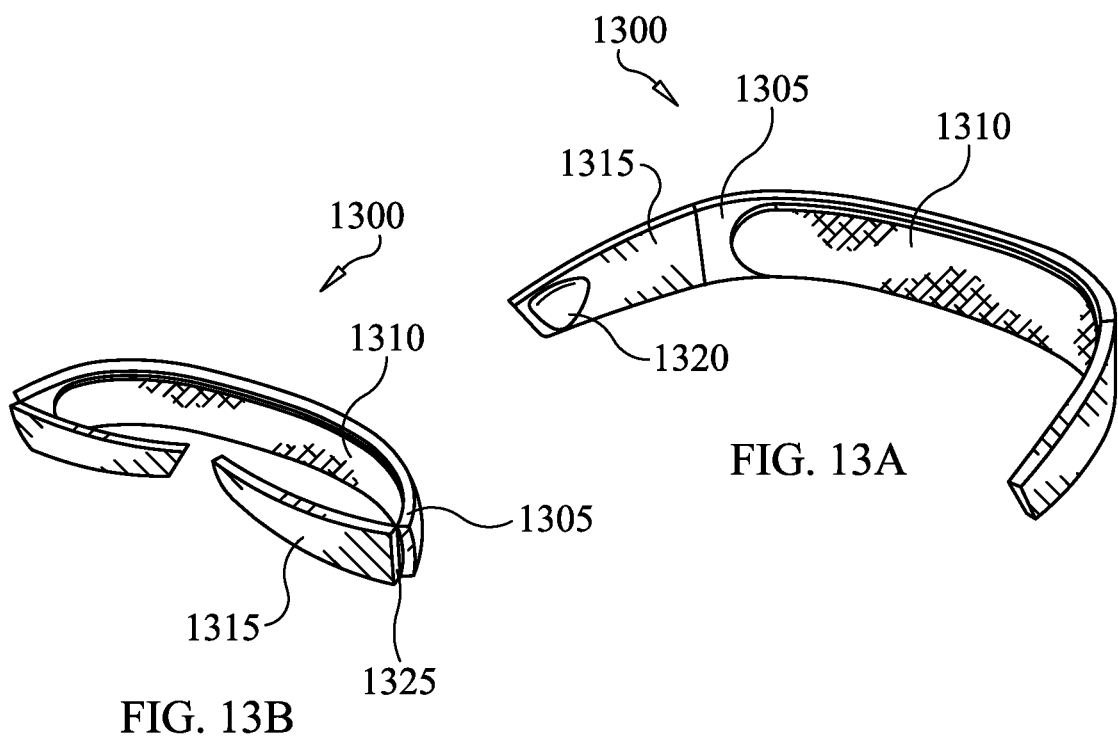
FIG. 13A
FIG. 13B

METHODS, DEVICES, SYSTEMS, AND KITS FOR REGULATING SKIN TEMPERATURE FOR MAMMALS TO INDUCE AND/OR MAINTAIN SLEEP

BACKGROUND

Traditional cold packs used to transfer heat from mammalian skin utilize either a chemical reaction or a refrigerator/freezer to chill a substance, which is usually water or gel. These packs are difficult to use because, for example, a refrigerator is not portable. Therefore, if a user wants a cold pack, he or she must travel to the refrigerator to extract the pack. Furthermore, the user has no control over the temperature of the cold pack other than by controlling the temperature of the refrigerator, which may not be convenient.

Traditional hot packs are problematic in that they typically require an electrical connection, as may be the case with a heating pad, and offer poor temperature regulation.

SUMMARY

Disclosed herein are methods, devices, systems, and kits for regulating skin temperature for mammals to, for example, inhibit metabolism in a subject's pre-frontal cortex in order to, for example, induce and/or maintain sleep.

In some embodiments, a pre-cooled heat transfer pack (temperature of, for example, 10° Celsius or below) on the subject's forehead so that the heat transfer pack is in thermal communication with the subject's forehead. Thermal communication between the subject's forehead and the heat transfer pack may be maintained for a period of time sufficient to cool the subject's pre-frontal cortex. The period of time may be a period of time sufficient to slow the metabolic rate of the subject's pre-frontal cortex and/or induce sleep.

In some embodiments, the heat transfer pack may not be coupled to a power source and/or cooling device when in contact with the subject's forehead. The heat transfer pack may be configured to warm, over time, when in thermal communication with the subject's forehead and may, in some instances, reach a homeostatic temperature with the subject.

In some embodiments two or more heat transfer packs may be used in tandem by the subject to cool the forehead/induce sleep. In these embodiments, the first heat transfer pack may warm and at some point during the night, the subject may wake up. Upon waking, the subject may put a second heat transfer pack on his or her forehead and maintain contact therebetween for at least 20 minutes and/or until sleep is induced.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 10-12 provide exemplary heat transfer devices, in accordance with some embodiments of the present invention;

FIGS. 13A-13D provide different views of another exemplary heat transfer devices, in accordance with some embodiments of the present invention;

DETAILED DESCRIPTION

Figure 1A:
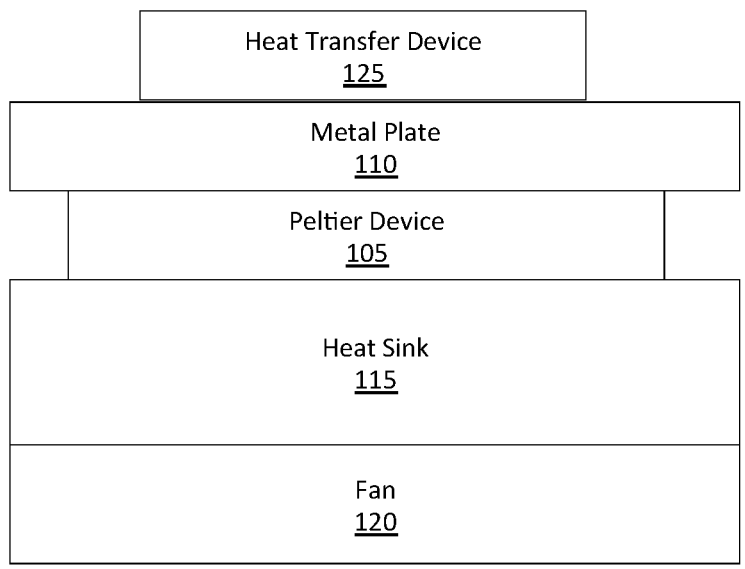
FIGS. 1A and 1B are block diagrams that illustrate exemplary heat transfer systems, in accordance with some embodiments of the present invention.

Disclosed herein is a system for cooling and/or heating the skin of a mammal (e.g., human being, cat, dog, horse, etc.). The system includes two fundamental components, a heat transfer machine and a heat transfer device. It is intended that the heat transfer machine be a machine that cools and/or heats the heat transfer device using a power supply (e.g., battery or electricity). Once the heat transfer device is heated and/or cooled, it may be removed from the heat transfer device and applied to the mammalian skin so as to heat and/or cool the mammalian skin. In most instances, the heat transfer device will be untethered to the heat transfer machine when applied to the mammal's skin. In one embodiment, the heat transfer machine is a tabletop device that may be placed on a user's nightstand so as to provide ready access to a chilled and/or heated heat transfer device during the night. In other embodiments, a heat transfer device may be used to regulate body temperature and may thusly provide comfort cooling for an individual that is not directed toward treatment of an injury as a traditional ice pack may be.

In most embodiments, the heat transfer device will rest on top of and/or outside of the heat transfer machine and/or a component of the heat transfer machine that provides heat transfer capability. When the heat transfer device is cooled, it may be cooled to a desired temperature of, for example, 1-9° C. The heat transfer device and/or a heat transfer pack situated thereon may be adapted to maintain a desired temperature when in contact with mammalian skin for a period of time (e.g., 20 minutes, 1 hour, 3 hours, etc.). The heat transfer pack's ability to maintain a desired temperature when in contact with the mammalian skin may be achieved by, for example, the use of desired materials and/or combinations of materials for the heat transfer device, heat transfer pack, and/or heat transfer machine.

Typically, heat transfer devices include a housing configured to house one or more heat transfer packs and may be adapted to be positioned on mammalian skin in a particular location. For example, a heat transfer device housing may be configured to be worn on a mammal's head, leg, ankle, knee, elbow, etc. Exemplary heat transfer device housings may be made from rigid, semi-rigid, and/or flexible materials and, in some instances, may include one or more fastening mechanisms (e.g., VELCRO™, clips, elastic, snaps, etc.). On some occasions, heat transfer device housings may include an insulation layer adapted to, for example, transfer heat to and/or from the mammalian skin more efficiently, absorb condensation or sweat, increase the comfort of wearing an heat transfer device, provide a source of friction between the heat transfer device and the mammal's skin so as to prevent movement and/or slipping of the heat transfer device from its desired location, etc.

Heat transfer packs may be any material configured to change temperature when placed in or on a heat transfer machine including, but not limited to, gel, cellulose solutions with a freezing point of approximately 32° F., silica gel solutions with an exemplary freezing point of approximately 25° F., a cryopak phase change material (PCM) with a freezing point of approximately 40° F., diethylene glycol with a freezing point between approximately 10° F. and 32° F., ethylene glycol with a freezing point between approximately 8° F. and 32° F., moldable clay, and water.

In some instances, heat transfer packs may be removable from the heat transfer device housing via one or more attachment mechanisms (e.g., glue, clips, VELCRO™, etc.). A user may desire to remove heat transfer packs from heat transfer device housing for any number of reasons including, but not limited to, replacement of a heat transfer packs, cleaning the heat transfer device, and changing a size of an heat transfer packs. In some instances, different heat transfer packs may have different features or qualities that may incorporate functional, comfort, and/or decorative features. For example, a first heat transfer packs may be configured to reach a first temperature when chilled by a heat transfer machine while a second heat transfer packs may be configured to reach a second temperature when chilled by the heat transfer machine.

Surfaces for heat exchange for a heat transfer machine may be made from, for example, polyurethane foam R-6.3, polystyrene R-4, aerogel with R values up to 105, thermally insulated glass, copper, aluminum, and combinations thereof.

FIG. 1A provides and exemplary heat transfer system 100, that employs a Peltier device 105, a metal plate 110, a heat sink 115, a fan 120, a heat transfer device 125, and a housing 130. Peltier device 105 may be a thermal electric cooler that uses an electrical power input to create a temperature differential at a junction between two types of materials. This differential creates a potential for heat transfer to occur across the junction. Using the Peltier device 105, there is a maximum amount of heat that can be removed from a metal plate 110 and every Peltier device 105 has an input power point at which it is most efficient at transferring heat. Increasing the input power past this point produces enough heat within the Peltier device to counteract some of the work completed by the heat transfer process. On the other hand, going below the power point does not produce the optimum amount of heat transfer, as expected.

Heat sink 115 may be used to draw heat away from the hot side of the Peltier device 105 junction to prevent the heat from accumulating within the Peltier device 105. Fan 120 may be used to dissipate some of the heat stored in heat sink 115 into the surrounding environment. The placement of the components of heat transfer system 100 in the configuration of FIG. 1A enables heat to be drawn from metal plate 110 into heat sink 115.

Figure 1B:
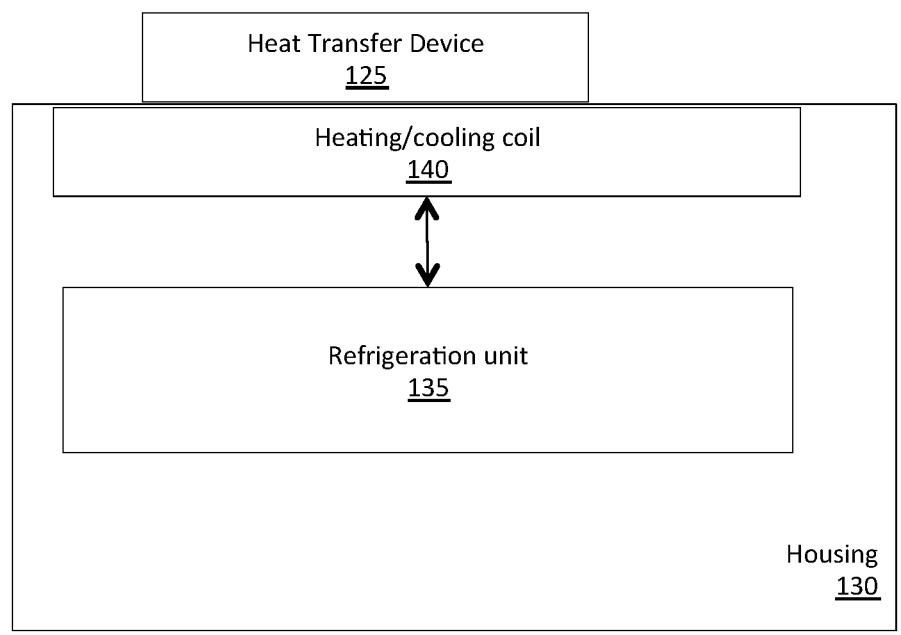

FIG. 1B provides another exemplary heat transfer system 101, which employs a housing 130, refrigeration unit 135 coupled to a cooling coil 140. The heating/cooling unit 135 and heating/cooling coil 140 are housed within housing 130 and an exemplary heat transfer device 125 is placed on an exterior surface of housing 130. In embodiments where heat transfer system 101 is designed to cool heat transfer device 125, h/c unit 135 may be a refrigeration unit that pumps cold liquid or gas through h/c coil 140 so that a portion of the exterior surface of housing 130 is cooled and heat may be transferred from heat transfer device 125 to housing 130 via placing heat transfer device 125 on housing 130. In embodiments where heat transfer system 101 is designed to heat transfer device 125, h/c unit 135 may be an electric heating coil or an induction heating device configured to warm the exterior surface of housing 120 and heat may be transferred to heat transfer device 125 to housing 130 via placing heat transfer device 125 on housing 130. In some embodiments, heat transfer system 101 may be configured to transfer heat both to and from heat transfer device 125 and these embodiments may include both a heating and a refrigeration apparatus.

Heat transfer systems 100 and/or 101 may be configured to be enclosed in a heat transfer machine. A heat transfer machine may be of any shape and/or size however, it will often be small enough to fit on, for example, a nightstand, a tabletop, or a counter in a user's residence. In most cases, heat transfer machine will be powered via a standard household electrical power supply although, in some instances, a battery that may be rechargeable may power heat transfer machine.

In some embodiments, the heat transfer machines described herein may be configured to monitor the state and/or temperature of a heat transfer device placed thereon and/or therein and may adjust one or more operations performed by a component of the heat transfer machine responsively to the monitoring. For example, when a heat transfer device has reached a desired temperature, heat transfer machine may be configured to turn off or cycle on and off so as to maintain the desired temperature of the heat transfer machine.

In other embodiments, a heat transfer machine and corresponding heat transfer device may be configured to couple to one another in a manner that limits heat transference to and/or from the external environment. For example, in some instances there may be an air-tight seal between an heat transfer machine and its corresponding heat transfer device and in other instances, an heat transfer machine and/or heat transfer device may include a gasket or other coupling mechanism configured to limit heat transference to and/or from the external environment In some instances, the heat transfer machines described herein are sized and shaped to accommodate inclusion of and one or more components of heat transfer systems 100 and/or 101 therein. Heat transfer systems 100 and/or 101 may transfer heat to and/or from a heat transfer device via, for example, conduction (e.g., placing a heat transfer device proximate to a hot or cold surface of heat transfer systems 100 and/or 101) and/or convection (e.g., using a fan to cool and/or heat an heat transfer device).

Figure 2:
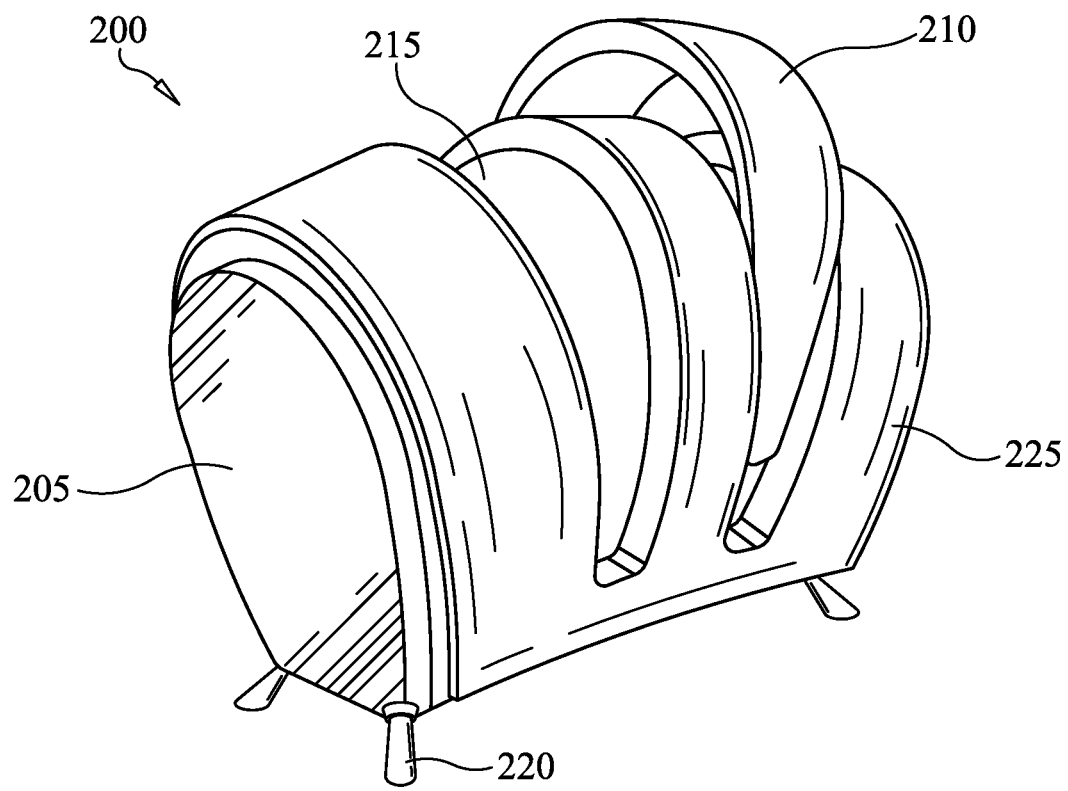
FIG. 2 provides a perspective view of an exemplary heat transfer machine, in accordance with some embodiments of the present invention.

Additionally, or alternatively, the heat transfer machines described herein may be sized and shaped to accommodate positioning of one or more different heat transfer devices thereon or therein. For example, FIG. 2 provides an heat transfer machine 200 that includes a ventilation grate 205, a removable headband-shaped heat transfer device 210, a heat exchange surface 215, a support 220, and an exterior housing 225 configured to accommodate the shape and size of removable headband-shaped heat transfer device 210, which in the embodiment of FIG. 2 is shaped like a headband. Exterior housing 225 is shaped with a flat bottom and a curved upper surface that corresponds to the curvature of the headband-shaped heat transfer device 210.

Heat exchange surface 215 may be configured to transfer heat to and/or from headband-shaped heat transfer device 210 and, in some instances, may correspond to, for example, metal plate 110 and/or housing 130. In some instances, heat exchange surface 215 may be a surface or layer of material positioned above metal plate 110 and/or housing 130. In these instances, heat exchange surface 215 may be, for example, plastic or metal. In some embodiments, heat exchange surface 215 may be designed so as to limit the accumulation of condensation thereon. For example, heat exchange surface 215 may include a water absorbing material such as foam or fabric.

Ventilation grate 205 may be shaped so as to fit on either side end of exterior housing 225. Ventilation grate 205 may be configured to allow the passage of air through the heat transfer machine 200 so as to, for example, cool a heat sink such as heat sink 115 and/or a refrigeration unit such as refrigeration unit 135. In some embodiments, ventilation grate 205 may have a decorative pattern.

Figure 3:
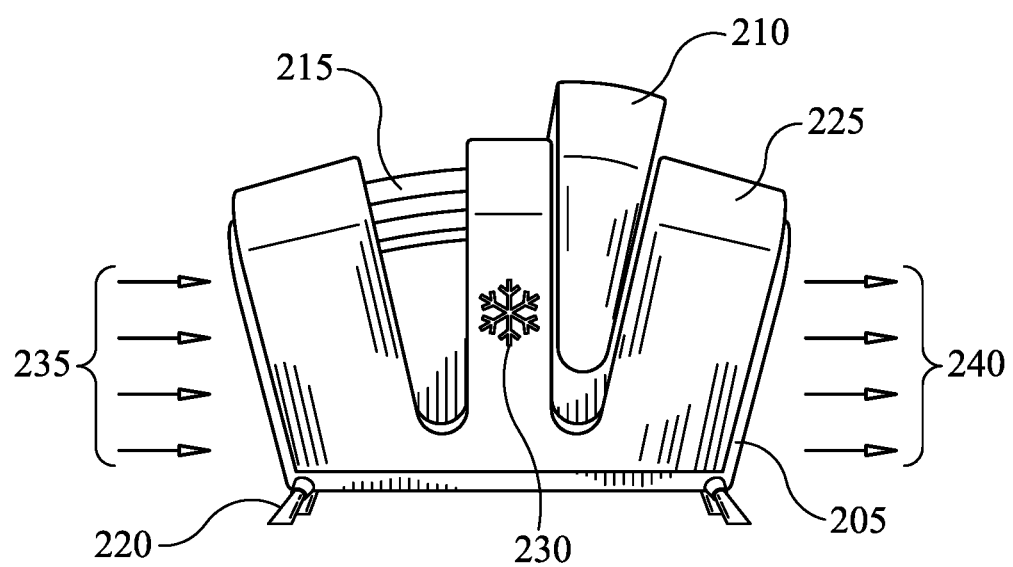
FIG. 3 provides a side plan view of an exemplary heat transfer machine, in accordance with some embodiments of the present invention.

FIG. 3 shows a side plan view of heat transfer machine 200. In this view of heat transfer machine 200, an indicator light 230 may be seen. Indicator light 230 may be configured to, for example, illuminate when a headband-shaped heat transfer device 210 is placed heat exchange surface 215 and/or when headband-shaped heat transfer device 210 has reached a desired temperature.

FIG. 3 also shows an incoming air flow 235 entering a first ventilation grate 205 and an outgoing air flow 240 as it second ventilation grate 205 of heat transfer machine 200 as may be the case when, for example, a fan, such as fan 120 draws air into heat transfer machine 200 so as to cool a heat sink, such a heat sink 115 and/or a refrigeration unit, such as refrigeration unit 135, and blows the air out of heat transfer machine 200.

Figure 4A:
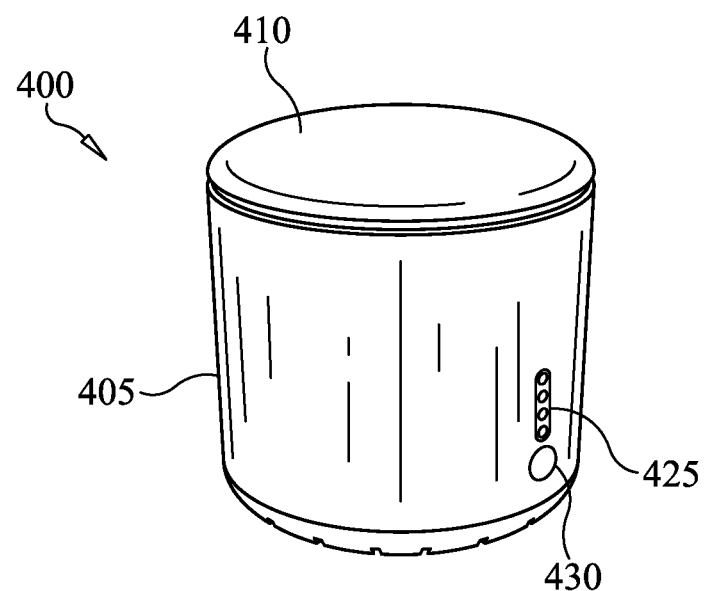
FIGS. 4A and 4B provide illustrations of an alternate exemplary heat transfer machine, in accordance with some embodiments of the present invention.
Figure 4B:
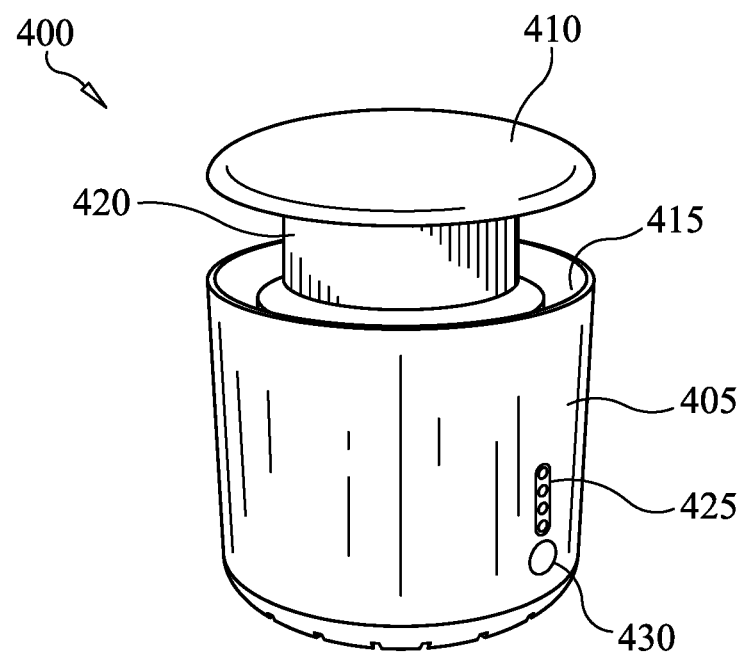

FIGS. 4A and 4B provide another exemplary heat transfer machine 400 that is substantially cylindrical in shape with a round cross section in at least one plane. FIG. 4A shows the heat transfer machine 400 when in a closed position and FIG. 4B shows the heat transfer machine 400 when in an open position. An exterior canister or container 405 provides a receiving space 415 into which a cooling canister 410 may be inserted. FIG. 4A shows the cooling canister 410 inserted into canister 405 (i.e., a closed position) and FIG. 4B shows the cooling canister 410 when extending from canister 405 (i.e., an open position).

A heat transfer system, such as heat transfer system 100 and/or 101 may be positioned within heat transfer machine 400 (not shown). In some embodiments, the heat transfer system may be positioned within cooling canister 405 and, in other embodiments, the heat transfer system may be posited within the receiving space 415 and cooling canister 410 may fit over top of, or otherwise be coincident with, the heat transfer system.

Cooling canister 410 provides a heat transfer device heat transfer site 420, which may be shaped to as to accommodate positioning of one or more heat transfer device therein and/or thereon. The heat transfer system included in heat transfer machine 400 may be configured to provide heat transfer capabilities to the heat transfer device heat transfer site 420 so as to heat and/or cool a heat transfer device (not shown) positioned thereon and/or therein.

Cooling canister 410 may serve to collect any condensation caused by, for example, cooling a heat transfer device and/or heat transfer device heat transfer site 420 by, for example, insulating the heat transfer device and/or heat transfer device heat transfer site 420 from the ambient air/environment and/or providing a condensation collection device (e.g., a tray). In some embodiments, one or more rubber seal(s) and/or gasket(s) between the cooling canister 410 and the exterior canister 405 may effect insulating the cooling canister 410 from the ambient air. The one or more rubber seal(s) and/or gasket(s) may also provide a snug fit between the exterior canister 405 and the cooling canister 410. Additionally, or alternatively an exterior surface of the exterior canister 405 may be textured to create a visual or tactile impression for the user.

Heat transfer device 400 may provide electronics that regulate the temperature of the cooling canister 410 and/or a heat transfer device placed thereon or therein. These electronics may be coupled to, for example, power on/off button 430 and/or a visual indicator 425. Power on/off button 430 may serve to power the heat transfer machine 400 on and/or off and visual indicator 425 may act to provide a visual indicator of, for example, the temperature and/or degree of readiness of the heat transfer device and/or the cooling canister 410. Visual indicator 425 may be, for example, a light that changes color, a series of lights, etc.

In many instances, heat transfer machine 400 may be used when a heat transfer device is placed in or on heat transfer device heat transfer site 420 when heat transfer machine is in an open configuration as shown in FIG. 4B and heat transfer machine 400 is then closed (as shown in FIG. 4A). For example, a headband-shaped heat transfer device and/or a heat transfer device to be placed in a housing may be placed in heat transfer device heat transfer site 420 when heat transfer machine is in an open configuration and then, when the heat transfer machine is placed in a closed configuration, heat transfer machine may begin transferring heat to and/or from the heat transfer device.

Figure 5:
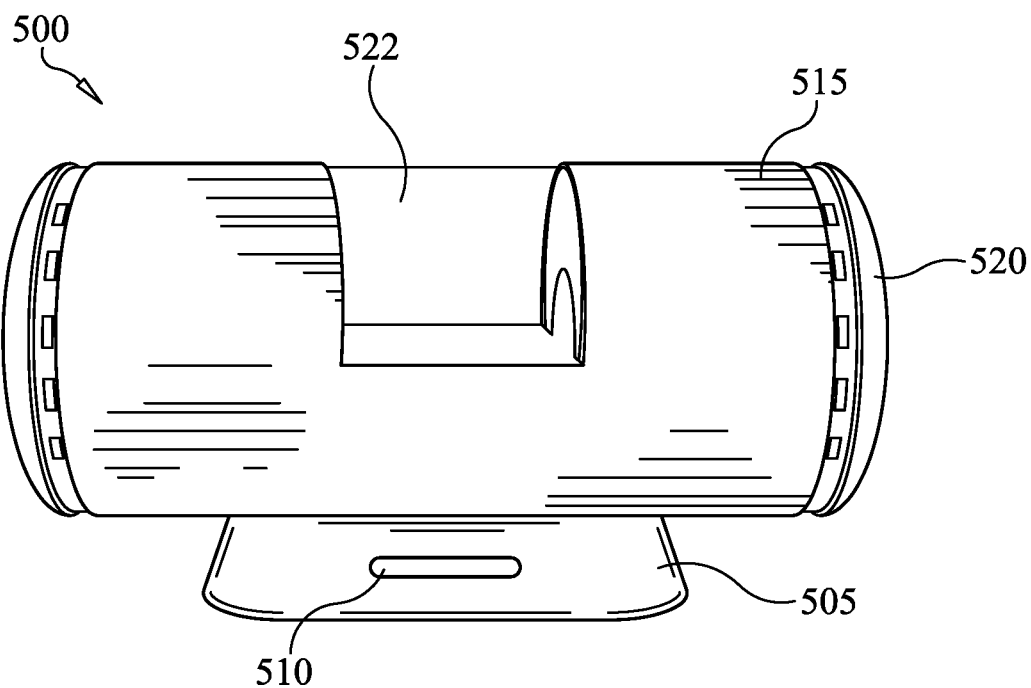
FIGS. 5-7 provide various views of an alternate exemplary heat transfer machine, in accordance with some embodiments of the present invention.
Figure 6:
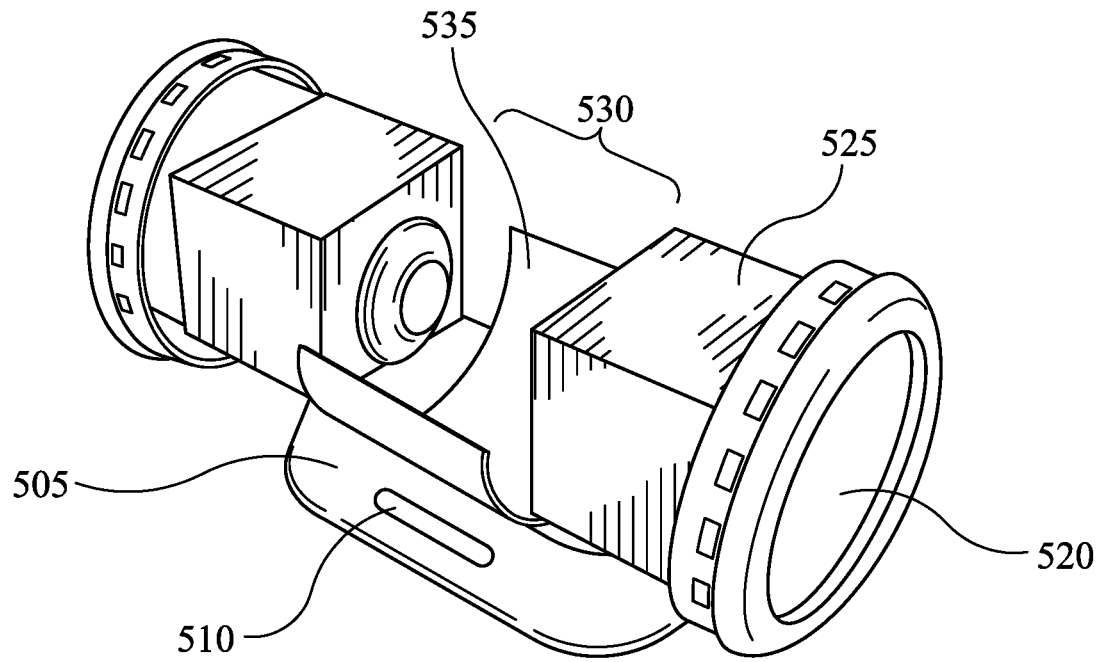
Figure 7:
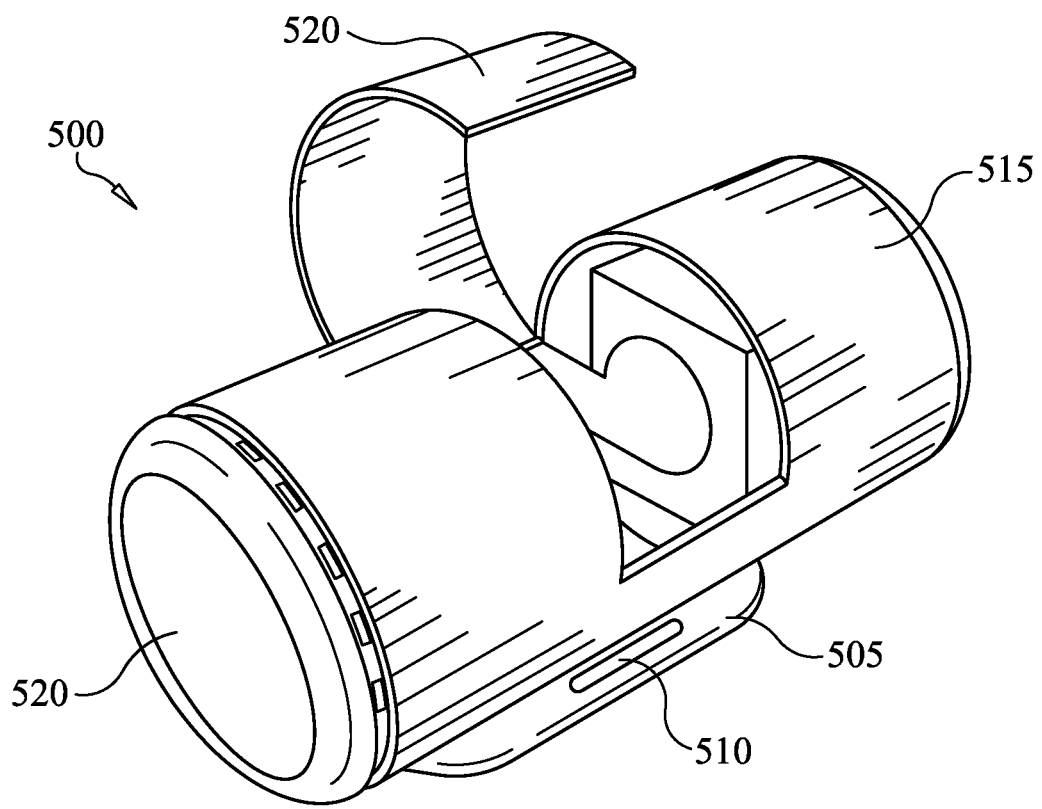

FIGS. 5-7 provide various views of an alternate exemplary heat transfer machine 500 with FIG. 5 being a front plan view of an assembled heat transfer machine 500 with a closed heat transfer device access door, FIG. 6 being a side perspective view of a partially assembled heat transfer machine 500, and FIG. 7 being a side perspective view of an assembled heat transfer machine 500 with an open heat transfer device access door. Heat transfer machine 500 includes a stand 505, a visual indicator 510, an exterior canister 515, an end cap 520, and a heat transfer device access door 522, an opening 530 to accommodate insertion and/or removal of an heat transfer device, a heat transfer surface 535, and heat transfer system components 525. Exterior canister 515 may house the components of heat transfer machine 500.

Heat transfer machine 500 may operate by opening heat transfer device access door 520, inserting a heat transfer device into opening 530 so that it is in contact with heat transfer surface 535, and closing the heat transfer device access door 520 and turning the heat transfer machine 500 on and/or setting a desired temperature for the heat transfer device placed in the heat transfer machine 500. Heat transfer system components 525 may act to change and/or regulate the temperature of heat transfer surface 535 according to, for example, one or more user-configured and/or default instructions in a manner similar to heat transfer machines 300 and 400.

Figure 8:
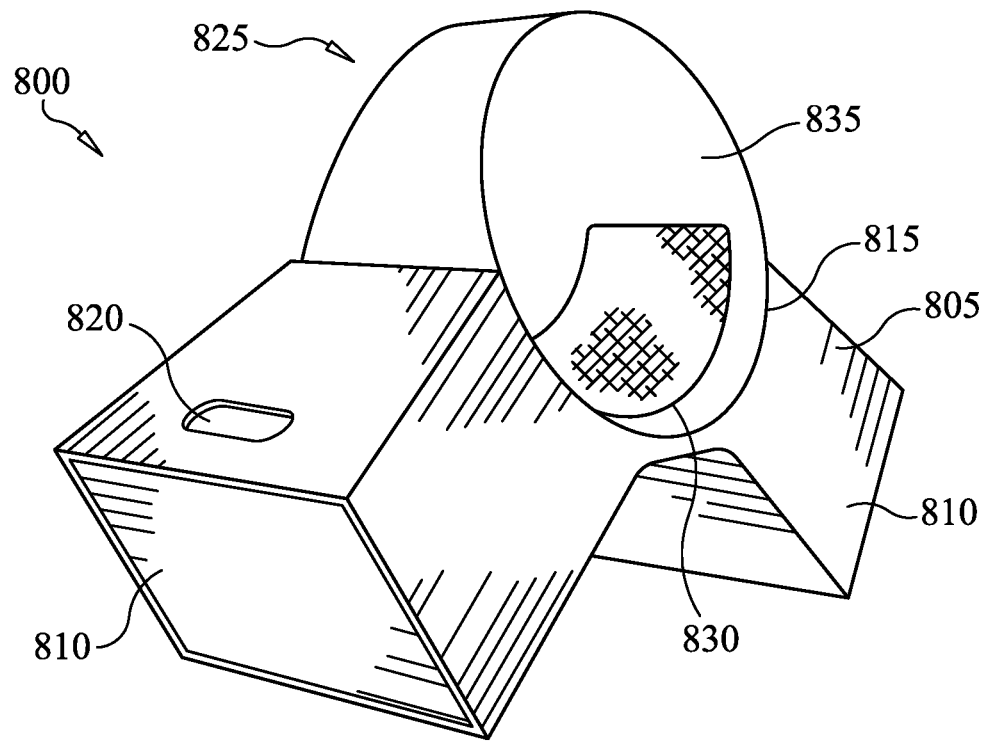
FIG. 8 is provides an exemplary heat transfer machine, in accordance with some embodiments of the present invention.

FIG. 8 shows yet another exemplary heat transfer machine 800 with an exemplary heat transfer device 825 placed thereon. Heat transfer machine 800 includes a base 805 with two legs oriented at an angle (e.g., 30-) 70° with respect to a surface upon which heat transfer machine 800 rests. Base 805 may house one or more heat transfer system 100 and/or 101 (not shown) that are configured to transfer heat to and/or from a heat transfer device 825 positioned within a cradle 815 provided by based 805. Cradle 815 may be sized and/or positioned to accommodate positioning of one or more heat transfer devices 825 thereon or therein. An exterior surface of cradle 815 may transfer heat to and/or from heat transfer device 825 positioned thereon/therein via conduction and/or convection.

Base 805 may include one or more ventilation grids 810 via which air may be pulled into and/or pushed out of base 805 by, for example, a fan included in heat transfer system 100 and/or 101. Base 805 may further include an indicator mechanism 820 that may serve to indicate to a user that the heat transfer machine 800 is on and/or off.

Heat transfer device 825 includes an exemplary heat transfer pack 830 and a heat transfer device housing 835. In the embodiment of FIG. 8, housing 835 has a circular shape that may be worn, for example, on a part of a mammal with a relatively large diameter/cross section (e.g., head, torso, upper leg, etc.) and heat transfer pack 830 is positioned on an interior surface of housing 835.

Figure 9:
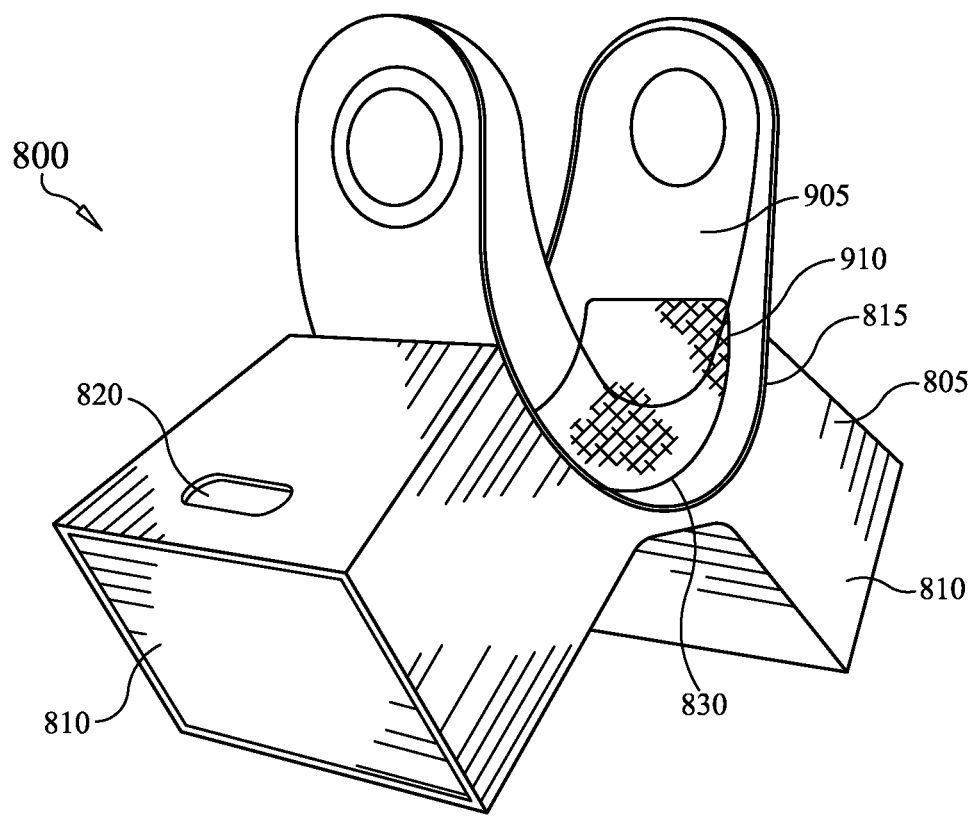
FIG. 9 is provides an exemplary heat transfer machine, in accordance with some embodiments of the present invention.

FIG. 9 shows heat transfer machine 800 with another exemplary heat transfer device 905 placed thereon. The housing 915 of heat transfer device 905 has a semicircular shape that may be conducive to use on a curved surface of mammalian skin (e.g., a head or leg). Heat transfer device 905 includes a heat transfer pack 910.

Figure 10:
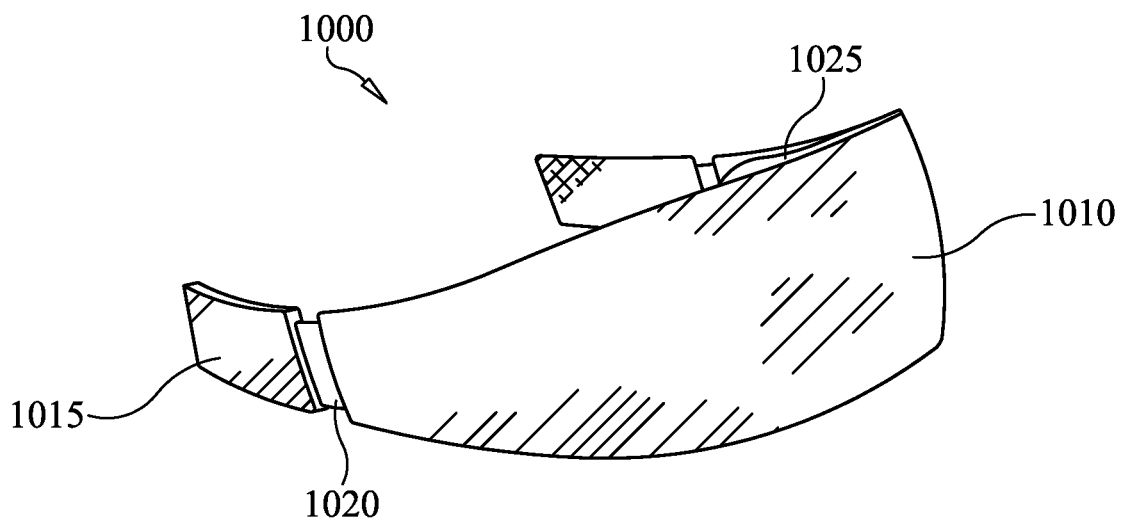
Figure 11:
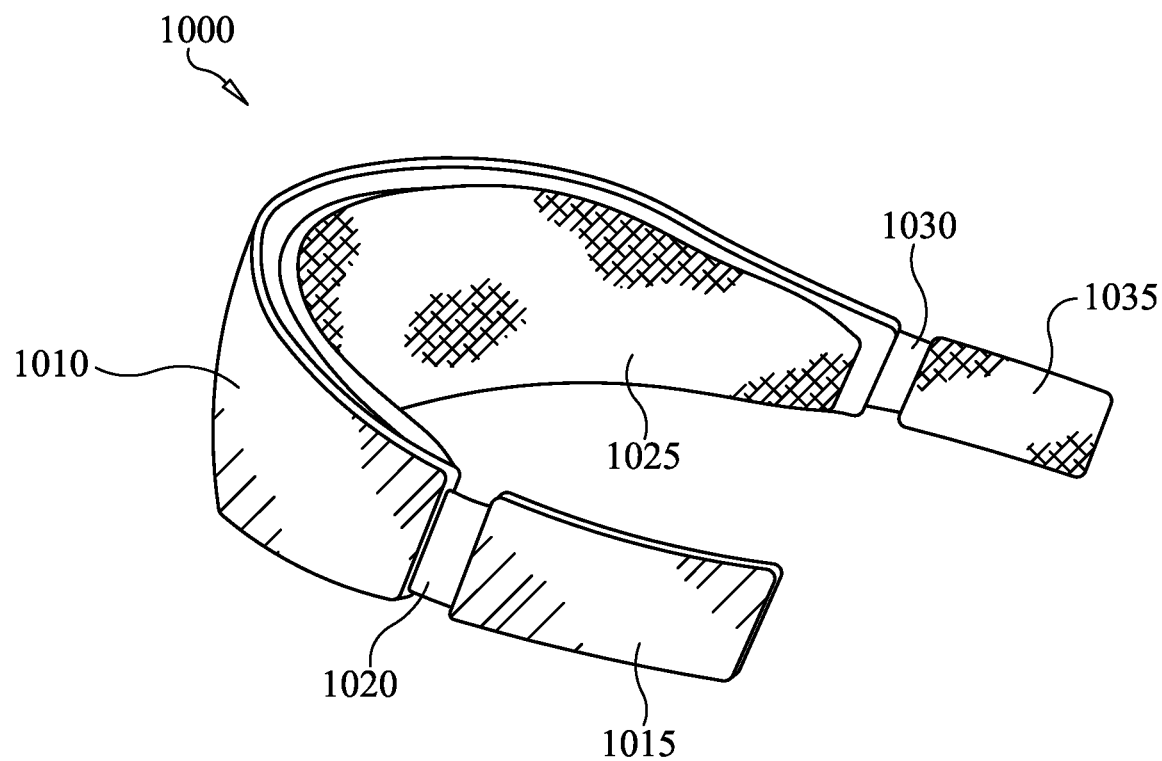

FIGS. 10-12 provide exemplary heat transfer devices 1000 configured to be worn on a person's head, and more specifically on across a person's forehead above the eyebrows and below the hairline. Heat transfer devices 1000 may include a housing 1010, two side extensions 1015, a slide bar 1020, a heat transfer pack 1025, a first liner 1030, and a second liner 1035. Housing 1010 may be configured to, for example, provide a structural shape to heat transfer devices 1000 and/or insulate the heat transfer pack from ambient air. First liner 1030 may be configured to provide padding to the heat transfer devices 1000 and assist conforming the shape of heat transfer devices 1000 to the shape of the person's head to which it is applied. Heat transfer pack 1025 may be designed to come into contact with a portion of the person's head and transfer heat to and/or from the person's skin and, in some instances, tissue underlying the skin.

One or more components of heat transfer devices 1000 may be adjustable so as to, for example, improve the fit of heat transfer devices 1000 when worn. For example, a positioning of side extensions 1015 may be adjusted and/or modified by sliding one, or both, side extensions 1015 away from and/or toward the main body of heat transfer devices 1000 along slide bar 1020. Second liner 1035 may act to facilitate comfortable compression of side extensions 1015 and/or housing 1010 onto a wearer's skin as shown in FIG. 12.

Figure 13C:
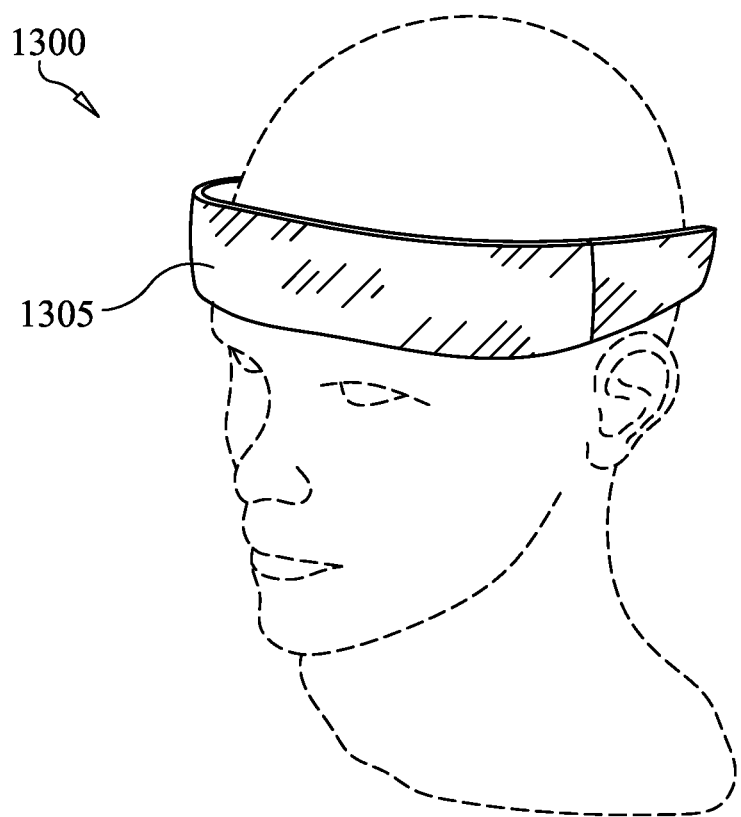

FIGS. 13A-13B provide different views of another exemplary heat transfer devices 1300 configured to be worn on a person's head, and more specifically on across a person's forehead above the eyebrows and below the hairline. Heat transfer devices 1300 may include a housing 1305, a heat transfer pack 1310, two side extensions 1315, a pad 1320, and a hinge 1325.

Figure 13D:
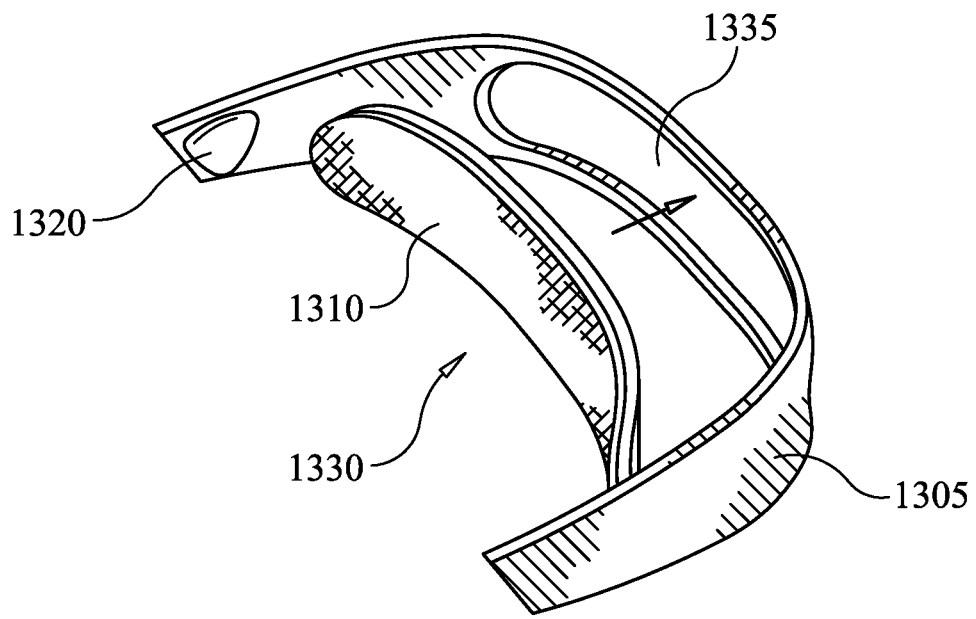

Housing 1305 may be configured to, for example, provide a structure and shape to heat transfer devices 1300 and/or insulate heat transfer pack 1310 from ambient air. As can be seen in FIG. 13D, heat transfer pack 1310 may be a component of an heat transfer pack assembly 1330 that may be removed from and/or inserted into housing 1305 via an opening 1335 in housing 1305. Heat transfer pack assembly 1330 may be removably affixed to housing 1305 via, for example, a friction mechanism or a mechanical structure such as a tongue and groove arrangement or a plurality of tabs or clips. Heat transfer pack assembly 1330 may be removed from housing 1305 so as to, for example, replace a first heat transfer pack assembly 1330 with a second Heat transfer pack assembly 1330 or to place heat transfer pack assembly 1330 in contact with a heat transfer machine as described above. In the embodiment of FIG. 13D, heat transfer pack assembly 1330 may include heat transfer pack 1310 and a layer of material that is the same as and/or similar to the material used to fabricate housing 1305.

Figure 14A:
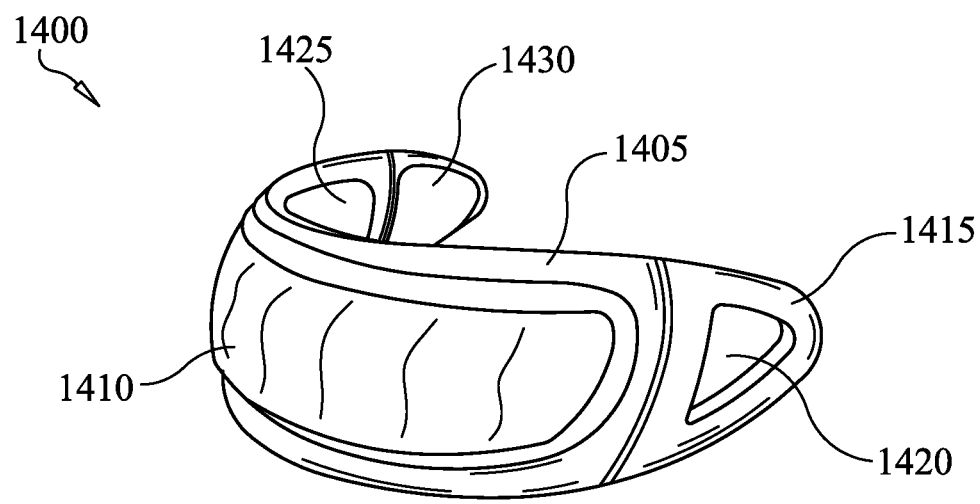
FIGS. 14A-14B provide different views of another exemplary heat transfer devices, in accordance with some embodiments of the present invention.
Figure 14B:
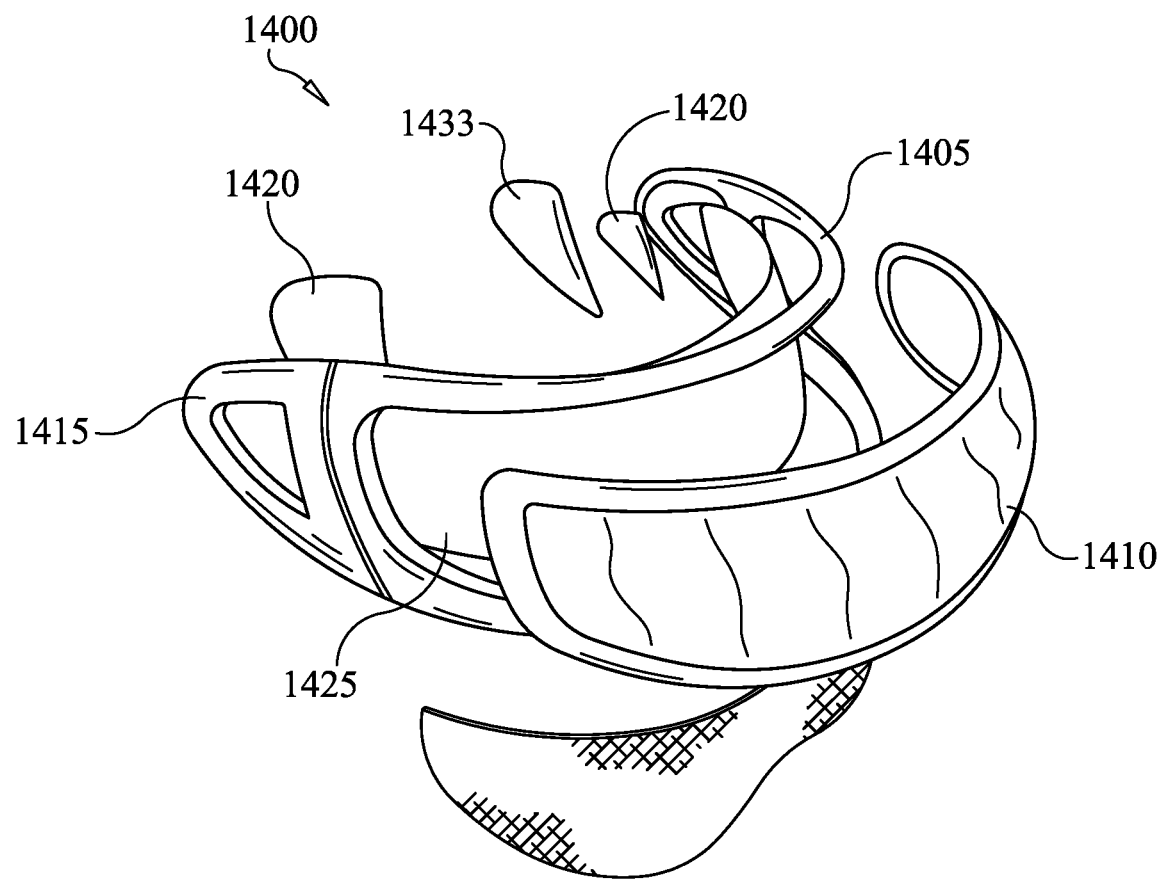

FIGS. 14A-14B provide different views of another exemplary heat transfer devices 1400 configured to be worn on, for example, a person's head or another curved surface of mammalian skin. Heat transfer devices 1400 may include a housing 1405, a first heat transfer pack 1410, two side extensions 1415, a second heat transfer pack 1420, a liner 1425, and a side pad 1430.

Housing 1405 may be configured to, for example, provide a structure and shape to heat transfer devices 1400, insulate heat transfer pack 1410 from ambient air, and/or provide a place in which to insert heat transfer pack 1410. Heat transfer pack 1410 may be removably affixed to housing 1405 via, for example, a friction mechanism or a mechanical structure such as a tongue and groove arrangement or a plurality of tabs or clips. Heat transfer pack 1410 may be removed from housing 1405 so as to, for example, replace a first heat transfer pack 1410 with a second heat transfer pack 1410 or to place heat transfer pack 1410 in contact with a heat transfer machine as described above. Heat transfer device 1400 includes a liner 1425 that may be adapted to insulate heat transfer pack 1410 from the heat of a mammal's skin to which it may be applied.

Figure 15A:
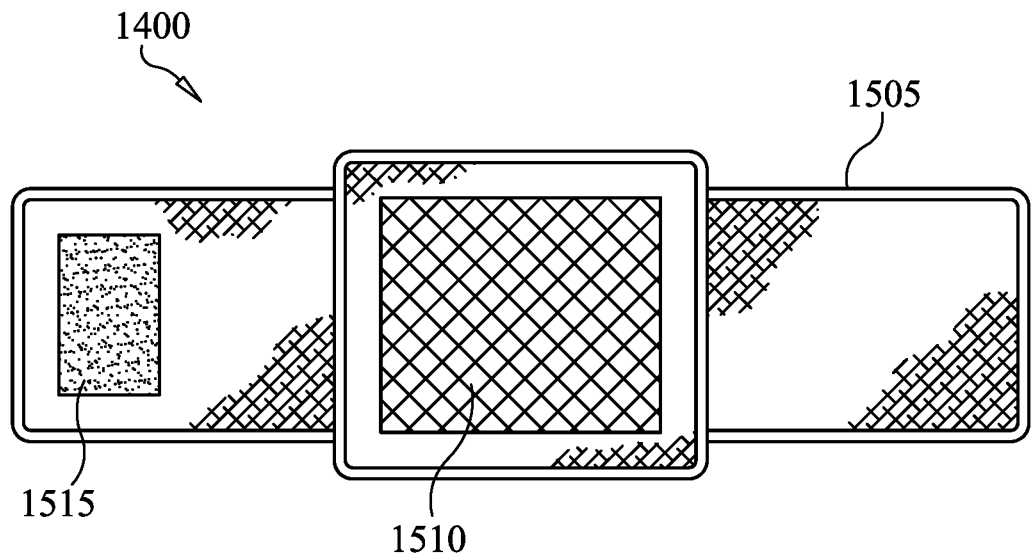
FIGS. 15A and 15B provide an exemplary heat transfer device, in accordance with some embodiments of the present invention.
Figure 15B:
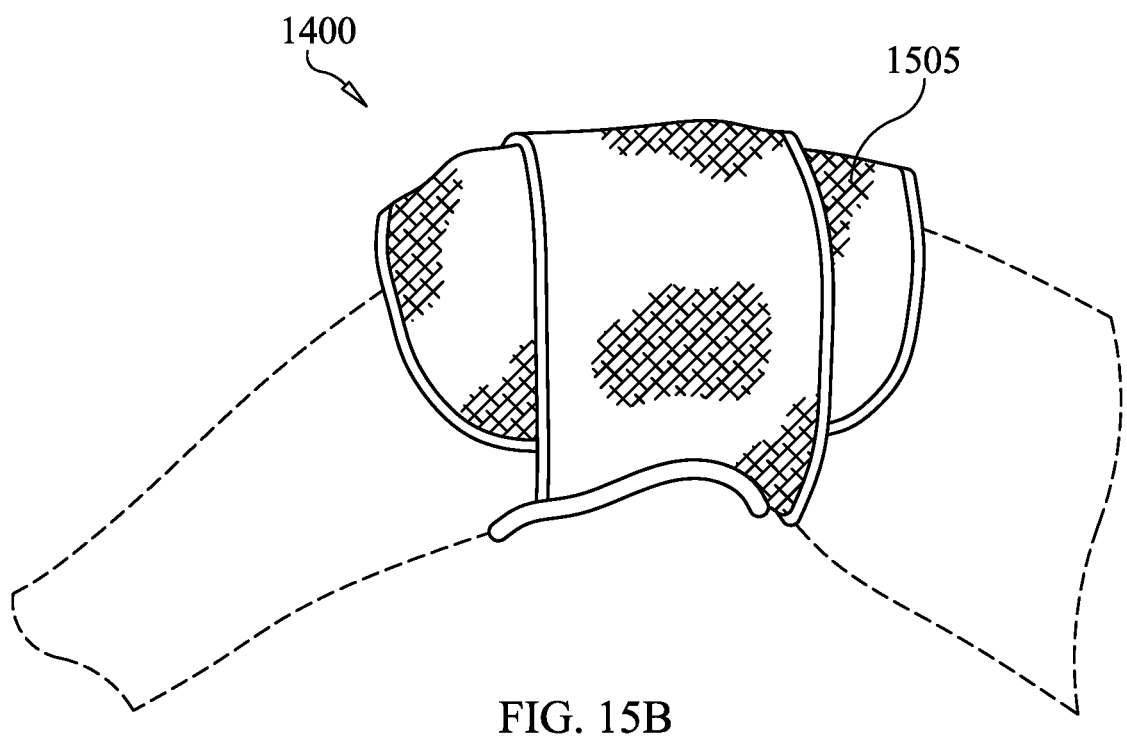

FIGS. 15A and 15B provide an exemplary heat transfer device 1500 in the form of a wrap for a mammalian limb (e.g., arm or leg) or torso that includes a housing 1505, a heat transfer pack 1510, and an attachment mechanism 1515. Heat transfer pack 1510 may be adapted to be cooled and/or heated via, for example, placement on a heat transfer device as described herein. In some embodiments, heat transfer pack 1510 may be removed from housing 1505 for heating/cooling via a heat transfer device and then affixed to and/or placed in housing 1505.

Housing 1505 may be used to, for example, facilitate placement of heat transfer pack 1510 on a desired body part and maintenance of the heat transfer pack's 1510 placement on the desired body part. In one example, the desired mammalian body part is a human knee. The housing 1505 may be employed to place the heat transfer pack in a desired position relative to the user's knee and wrap around the user's knee. Heat transfer device 1500 may be held in place via attachment mechanism 1515 as shown in FIG. 15B.

Figure 16:
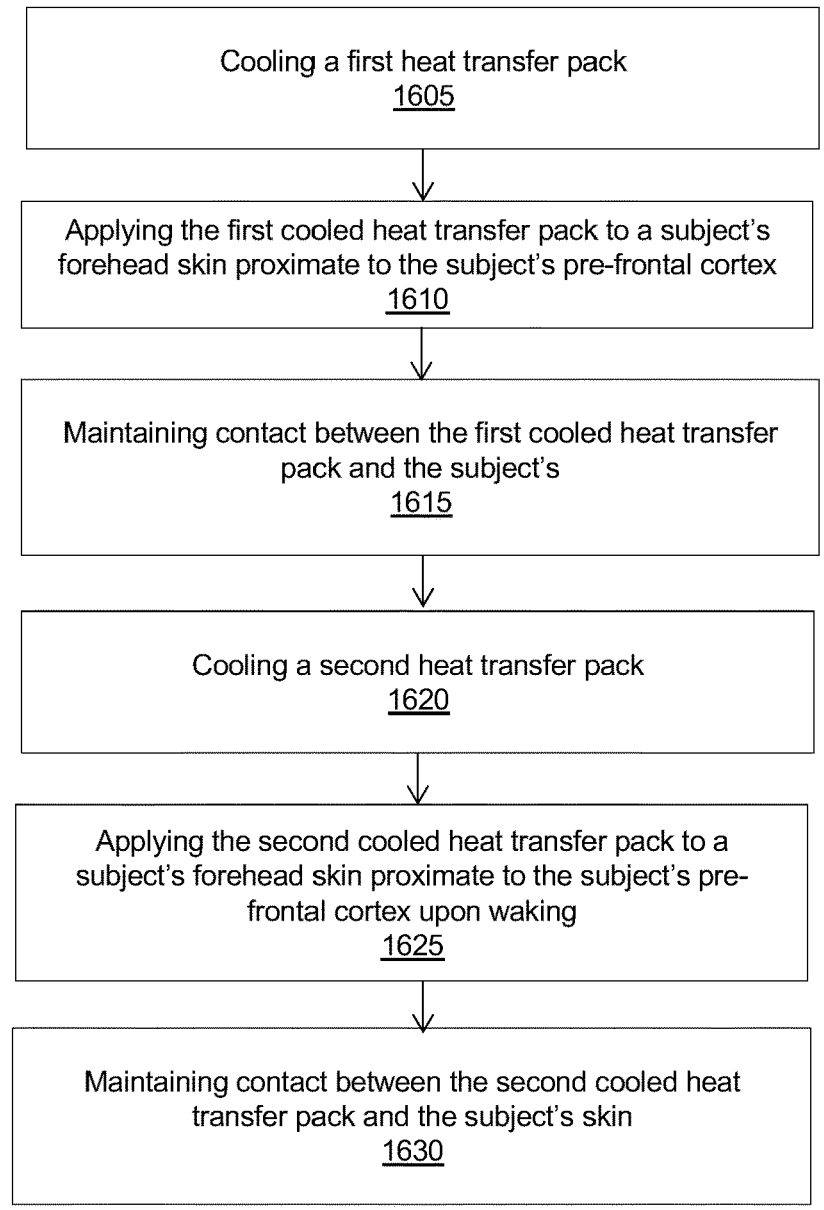
FIG. 16 is a flowchart illustrating an exemplary process for cooling, or reducing the temperature of, a subject's forehead and pre-frontal cortex.

FIG. 16 is a flowchart illustrating an exemplary process 200 for cooling, or reducing the temperature of a subject's forehead and pre-frontal cortex. Process 1600 may be performed using, for example, any of the systems or devices disclosed herein.

Initially, in step 1605, a heat transfer pack like heat transfer packs 830, 910, 1025, 1310, 1410, and/or 1510 may be cooled using, for example, heat transfer machine like heat transfer machine 200, 400, 500, and/or 800, 200, and/or a heat transfer system like heat transfer system 100 and/or 101 via, for example, conduction. The heat transfer pack may be cooled to a temperature of, for example, 10° Celsius or below. In some embodiments, the heat transfer pack of step 1605 may be a first of a plurality of heat transfer packs that are cooled. In some embodiments, the first heat transfer pack may be positioned on an external surface of the heat transfer machine. The first heat transfer pack may not be coupled to a power supply.

Then, in step 1610, the cooled heat transfer pack may be applied to the subject's forehead so that the heat transfer pack is in thermal communication with the subject's forehead so that heat may be transferred away from the subject's for head and/or tissue underlying the subject's skin (e.g., skull and pre-frontal cortex). Contact between the subject's forehead and the heat transfer pack and/or thermal communication between the subject's forehead may be maintained for a period of time sufficient to cool (i.e., reduce a temperature) the subject's pre-frontal cortex (step 1615). In some cases, the first heat transfer pack may be configured to lower the temperature of the pre-frontal cortex so that a metabolic rate of the pre-frontal cortex is lowered and an onset of sleep is induced.

Contact may be maintained via, for example, a heat transfer device like heat transfer device 125, 210, 400, 825, 905, 1000, 1300, and/or 1400. The thermal communication between the subject's forehead and the first heat transfer pack may induce the onset of sleep for the subject. In some embodiments, the first heat transfer pack is not thermally and/or electrically coupled to the heat transfer machine when in thermal communication with the subject's forehead.

In some embodiments, the first heat transfer pack may be configured to maintain its pre-cooled temperature for a period of time (e.g., 20 minutes, 40 minutes, 1, 2, 3, 4, hours) after which time the heat transfer pack may increase in temperature. In some embodiments, that heat transfer pack may include a phase change material which may change face from, for example, a solid to a semisolid (e.g., gel) and/or liquid during this period of time as he is transferred away from the subject's four head into the heat transfer pack. In some embodiments, the heat transfer pack may be configured to maintain the temperature to which it was cooled in step 1605 for no more than three hours when in contact with the subject's skin. The thermal communication between the subject's forehead and the second heat transfer pack may induce the onset of sleep for the subject.

In some embodiments, a temperature of the first heat transfer pack may be configured to increase while in contact with the subject's skin to gradually achieve a temperature of 20° Celsius or higher, eventually reaching, in some cases, homeostasis with the subject's forehead skin.

In some embodiments, a subject may wake up from sleep following an undesired duration sleep as my happen when, for example, the subject suffers from insomnia or other sleep-related disorders. In step 1625, the subject may apply a second heat transfer pack that has been cooled in step 1620 upon, for example, waking up following and undesirably short duration of sleep. The second heat transfer pack may be similar to the first heat transfer pack and may be cooled in a manner similar to execution of stub 1605. Contact between the second cooled heat transfer pack and the subject's skin may be maintained (step 1630).

In some embodiments, thermal communication between the subject's forehead and the first and/or second heat transfer pack may be maintained for a period of time sufficient to slow the metabolic rate of the subject's pre-frontal cortex, which may reduce the subject's ability to think and/or stay awake.

In some embodiments, application of the first heat transfer pack may cool the pre-fontal cortex and induce an onset of sleep. As the subject sleeps, the first heat transfer pack may warm (increase in temperature) eventually reaching homeostasis with the subject's body temperature. Upon the subject's waking from the sleep induced by application of the first heat transfer pack to the subject's forehead, the second cooled heat transfer pack may be applied to the subject's forehead skin proximate to the subject's pre-frontal cortex. Often times, the subject's forehead will have warmed to reach homeostasis so that the second heat transfer pack, when applied, is colder than the subject's body temperature. In this way, the subject's head may be re-cooled by the second heat transfer pack and contact between the second cooled heat transfer pack and the subject's forehead skin proximate to the subject's pre-frontal cortex may be maintained for a period of time (e.g., 20 minutes or one hour) thereby inducing sleep.

Additionally, or alternatively, the first heat transfer pack may warm while the subject is asleep to, for example, a temperature of 30° Celsius or above. Upon the subject's waking from sleep induced by application of the first heat transfer pack to the subject's forehead, a second cooled heat transfer pack may be non-invasively applied to the subject's forehead skin proximate to the subject's pre-frontal cortex. Contact between the second cooled heat transfer pack and the subject's forehead skin proximate to the subject's pre-frontal cortex may be maintained thereby inducing an onset of sleep.

Additionally, or alternatively, in some embodiments, process 1600 may be executed by, for example, cooling a heat transfer pack to a desired temperature with a heat transfer machine to a temperature of, or below, 10° Celsius, non-invasively applying the cooled heat transfer pack to a subject's forehead skin proximate to the subject's pre-frontal cortex and maintaining contact between the cooled heat transfer pack and the subject's forehead skin proximate to the subject's pre-frontal cortex for at least 20 minutes.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

I claim:

1. A method of cooling a subject's forehead, the method comprising:

positioning a first pre-cooled heat transfer pack on the subject's forehead so that the heat transfer pack is in thermal communication with the subject's forehead, an initial temperature of the pre-cooled heat transfer pack being below 10° Celsius;

maintaining thermal communication between the subject's forehead and the heat transfer pack for a first period of time sufficient to cool a pre-frontal cortex of the subject and induce a first onset of sleep;

positioning a second pre-cooled heat transfer pack on the subject's forehead so that the heat transfer pack is in thermal communication with the subject's forehead responsively to a determination that the subject has awoken from sleep induced by application of the first pre-cooled heat transfer pack to the subject's forehead, an initial temperature of the second pre-cooled heat transfer pack being below 10° Celsius;

maintaining thermal communication between the subject's forehead and the second pre-cooled heat transfer pack for a second period of time sufficient to cool the pre-frontal cortex of the subject and induce a second onset of sleep.

2. The method of claim 1, the thermal communication between the subject's forehead and a first and second heat transfer pack is maintained for a period of time sufficient to slow the metabolic rate of the subject's pre-frontal cortex.

3. The method of claim 1, wherein at least one of the first and second heat transfer packs comprise one or more phase change materials.

4. The method of claim 1, wherein at least one of the first and second periods of time is at least 20 minutes in duration.

5. The method of claim 1, wherein at least one of the first and second heat transfer packs maintain a temperature to which it was pre-cooled for no more than 30 minutes when in contact with the subject's skin.

6. The method of claim 1, wherein at least one of the first and second heat transfer packs is not coupled to a power supply.

7. The method of claim 1, wherein a temperature of at least one of the first and second heat transfer packs is configured to increase while in contact with the subject's skin.

8. The method of claim 1, wherein at least one of the first and second heat transfer packs is configured to change temperature over time while in contact with the subject's skin to gradually achieve a temperature of between 30° and 40° Celsius.

9. The method of claim 1, wherein at least one of the first and second heat transfer packs is configured to lower the temperature of the pre-frontal cortex so that a metabolic rate of the pre-frontal cortex is lowered and an onset of sleep is induced.

10. The method of claim 1, wherein at least one of the first and second heat transfer packs is pre-cooled when not in contact with the subject's forehead via thermal coupling to a heat transfer machine and further wherein the at least one of the first and second heat transfer packs is not in thermal communication with the heat transfer machine while in contact with the subject's forehead.

11. A method of non-invasively cooling a subject's pre-frontal cortex comprising:

cooling a first heat transfer pack to a desired temperature with a heat transfer machine, the desired temperature being below 10° Celsius;

non-invasively applying the first cooled heat transfer pack to a subject's forehead skin proximate to the subject's pre-frontal cortex; and maintaining contact between the cooled first heat transfer pack and the subject's forehead skin proximate to the subject's pre-frontal cortex for at least 20 minutes thereby inducing a first onset of sleep;

cooling a second heat transfer pack to a desired temperature with a heat transfer machine, the desired temperature being below 10° Celsius;

non-invasively applying the second cooled heat transfer pack to the subject's forehead skin proximate to the subject's pre-frontal cortex responsively to a determination that the subject has awoken from sleep induced by application of the first heat transfer pack to the subject's forehead; and maintaining contact between the second cooled heat transfer pack and the subject's forehead skin proximate to the subject's pre-frontal cortex for at least 20 minutes thereby inducing a second onset of sleep.

12. The method of claim 11, wherein the contact between the first heat transfer pack and the subject's forehead and at least one of the first and second heat transfer packs is maintained for a period of time sufficient to slow a metabolic rate of the subject's pre-frontal cortex.

13. The method of claim 11, wherein at least one of the first and second heat transfer packs is not thermally coupled to the heat transfer machine when in thermal communication with the subject's forehead.

14. The method of claim 11, wherein at least one of the first and second heat transfer packs comprises one or more phase change materials.

15. The method of claim 11, wherein at least one of the first and second heat transfer packs maintains a temperature to which it was pre-cooled for no more than three hours when in contact with the subject's skin.

16. The method of claim 11, wherein at least one of the first and second heat transfer packs is not coupled to a power supply.

17. The method of claim 11, wherein a temperature of at least one of the first and second heat transfer packs is configured to increase while in contact with the subject's skin.

18. The method of claim 11, wherein at least one of the first and second heat transfer packs is configured to change temperature over time while in contact with the subject's skin to gradually achieve a temperature of 30° Celsius.

19. The method of claim 11, wherein the contact between at least one of the first and second heat transfer packs and the subject's forehead skin proximate to the subject's pre-frontal cortex reduces a temperature of the subject's pre-frontal cortex.

20. The method of claim 11, wherein at least one of the first and second heat transfer packs is configured to lower a temperature of the pre-frontal cortex so that a metabolic rate of the pre-frontal cortex is lowered and an onset of sleep is induced.

21. The method of claim 11, wherein at least one of the first and second heat transfer packs is cooled when not in contact with the subject's forehead via thermal coupling to the heat transfer machine and further wherein the at least one of the first and second heat transfer packs is not in thermal communication with the heat transfer machine while in contact with the subject's forehead.

* * * * *